(12) United States Patent
Cox

(10) Patent No.: US 8,699,037 B2
(45) Date of Patent: Apr. 15, 2014

(54) HOLE INSPECTION

(75) Inventor: Peter J. Cox, Coventry (GB)

(73) Assignee: Rolls-Royce PLC, London (GB)

( * ) Notice: Subject to any disclaimer, the term of this patent is extended or adjusted under 35 U.S.C. 154(b) by 183 days.

(21) Appl. No.: 13/252,459

(22) Filed: Oct. 4, 2011

(65) Prior Publication Data

US 2012/0092681 A1 Apr. 19, 2012

(30) Foreign Application Priority Data

Oct. 15, 2010 (GB) .................................. 1017506.5

(51) Int. Cl.
| | |
|---|---|
| *G01B 11/00* | (2006.01) |
| *G01N 21/954* | (2006.01) |
| *G01B 11/22* | (2006.01) |
| *G01B 11/12* | (2006.01) |
| *G01B 11/08* | (2006.01) |
| *G01N 3/42* | (2006.01) |

(52) U.S. Cl.
CPC .............. *G01N 21/954* (2013.01); *G01B 11/22* (2013.01); *G01B 11/12* (2013.01); *G01B 11/08* (2013.01); *G01N 3/42* (2013.01)
USPC ................. 356/626; 356/237.137; 356/237.6; 356/600; 356/241.1; 356/241.6

(58) Field of Classification Search
CPC ........ G01B 11/22; G01B 11/12; G01B 11/02; G01B 11/08; G01N 3/42
USPC ........ 356/626, 600–614, 237.1–237.6, 241.1, 356/241.6
See application file for complete search history.

(56) References Cited

U.S. PATENT DOCUMENTS

| | | | | | |
|---|---|---|---|---|---|
| 5,197,105 | A | * | 3/1993 | Uemura et al. | 382/147 |
| 5,902,232 | A | * | 5/1999 | Igarashi | 600/176 |
| 5,909,284 | A | * | 6/1999 | Nakamura | 356/635 |
| 6,198,102 | B1 | * | 3/2001 | Shepherd | 250/340 |
| 6,663,560 | B2 | * | 12/2003 | MacAulay et al. | 600/160 |
| 7,281,860 | B2 | * | 10/2007 | Fujita | 385/88 |
| 8,040,529 | B2 | * | 10/2011 | Okuda et al. | 356/614 |
| 2004/0097790 | A1 | | 5/2004 | Farkas et al. | |
| 2004/0165759 | A1 | | 8/2004 | Baldwin | |
| 2007/0197911 | A1 | | 8/2007 | Kaiser et al. | |
| 2009/0237677 | A1 | * | 9/2009 | Aoki et al. | 356/602 |

OTHER PUBLICATIONS

Feb. 1, 2011 Search Report issued in British Patent Application No. 1017506.5.

* cited by examiner

*Primary Examiner* — Tarifur Chowdhury
*Assistant Examiner* — Isiaka Akanbi
(74) *Attorney, Agent, or Firm* — Oliff PLC

(57) ABSTRACT

An apparatus is provided for inspecting holes in components. The apparatus includes a telecentric lens system positionable at a near end of a hole with an optical axis of the lens system aligned with the axis of the hole to image the interior of the hole. The apparatus further includes an illumination system for illuminating the interior of the hole. The apparatus further includes a camera arranged to receive an image of the illuminated interior of the hole from the telecentric lens system. The illumination system includes a light source for producing a beam of parallel light, and optics for directing the produced beam through the telecentric lens system along the optical axis thereof, and through the hole. The beam reaches the far end of the hole, and is reflected from a surface located at or adjacent the far end of the hole to illuminate the interior of the hole.

20 Claims, 3 Drawing Sheets

HOLE INSPECTION

The present invention relates to an apparatus and method for inspecting holes in components.

It is known to drill holes in components, e.g. using high energy beams such as laser beams or by electro discharge machining (EDM). In an aerospace gas turbine engine, components that may have drilled holes are high pressure turbine blades, nozzle guide vanes, fuel injectors and combustors, the drilled holes typically being used to transport flows of cooling air. Generally such holes have diameters in the range from 0.1 to 1.0 mm and lengths of from 2 to 20 mm.

When the hole is formed it can breakthrough to the opposing side of the component. It is often necessary to inspect holes for diameter and breakthrough condition.

FIG. 1 shows schematically a conventional apparatus for inspecting holes using optics and a camera in conjunction with vision inspection software to obtain information on the position and size of a hole at or adjacent an accessible end of the hole. An imaging system 3, which can be non-telecentric or telecentric, is positioned above an accessible, exterior end of the hole 2 in a component 1, with the optic axis of the imaging system aligned with the axis of the hole. The entrance to the hole is illuminated (indicated by dashed arrows) with light from a ring light 4 (typically an array of LED's or fibre optic ringlight) which surrounds the end of the imaging system. A camera 5 receives the image obtained by the imaging system and sends the image to a computer 6 running vision software. A monitor 7 can also display the image.

Often, however, the opposite end of the hole is inaccessible. For example, the hole may open to an internal cavity 8 within the component. A drawback of the conventional apparatus is then that the illuminating light may not penetrate to the opposite end, making it difficult to inspect the hole diameter at that end and also difficult to verify the extent of hole breakthrough to the internal cavity.

FIG. 2 shows schematically an alternative conventional apparatus for inspecting holes. The apparatus has a light probe 9 (typically in the form of a light-emitting sphere) controlled by a control unit 10 which communicates with the computer 6. The probe is lowered into the hole to the required depth for measurements. The probe is moved against the sidewall surface of the hole 2, and the extreme position of the probe is tracked using the imaging system 3, camera 5, computer 6 and display 7. In particular, by moving the probe laterally within the hole to several positions at the same depth the size of the hole at that depth can be determined using the vision software.

Another contact approach to hole inspection replaces the light probe 9 with a contact probe, the size of the hole being determined by the movements required to produce contact of the probe with the sidewall surface of the hole.

A drawback of probing approaches is that they are relatively slow due to the time required to manipulate the probe, and may not highlight breakthrough anomalies. Additionally the probe can be damaged by unintentional contact with a component.

GB A 2455538 proposes a method of detecting breakthrough in a laser drilling operation in which a stop-off material is provided on the opposing side of the component to which the laser is directed. An optical sensor generates a spectral wavelength signal from the process light which is reflected when the laser is incident on the component. Breakthrough is determined when a change occurs in the spectral wavelength signal that indicates that process light is being reflected from the stop-off material.

JP 2008-102011 A proposes a hole inside inspection device in which laser light is used to irradiate a hole, a CCD camera receiving the laser light from the hole without the aid of an objective lens.

The present invention is at least partly based on the realisation that surfaces at or adjacent the inaccessible ends of holes in components may be used to illuminate the interior of the hole Accordingly, the present invention provides a method of inspecting at least one hole in a component, the method comprising:

positioning a telecentric lens system at a near end of a hole with an optical axis of the lens system aligned with the axis of the hole, directing a beam of parallel light through the telecentric lens system along the optical axis thereof, and through the hole, such that the beam reaches a distal end of the hole, and is reflected from a surface located at or adjacent the distal end of the hole to illuminate the interior of the hole, receiving an image of the illuminated interior of the hole from the telecentric lens system, measuring at least one diameter and/or an area of the hole from the image of the illuminated interior of the hole, and determining the difference between the measured diameter and/or area of the hole and a diameter and/or area of a nominally acceptable hole.

The method may have any one or, to the extent that they are compatible, any combination of the following optional features.

The method step of measuring the diameter and/or an area of the hole may further comprise measuring two or more diameters of the hole and determining the average of the two or more diameters of the hole.

The two diameters may be perpendicular to one another.

The method step of measuring the diameter and/or an area of the hole may further comprise measuring ten or more diameters of the hole and determining the average of the ten or more diameters of the hole.

The method step of measuring the diameter and/or an area of the hole may further comprise measuring approximately fifty diameters of the hole and determining the average of the approximately fifty diameters of the hole.

The method may further comprise the step wherein the hole is rejected if the difference between the diameter and/or area of the hole and the diameter and/or area of the nominally acceptable hole is larger than a pre-determined rejection tolerance of the diameter and/or area.

The pre-determined rejection tolerance may be ±20%.

The method may further comprise the step wherein the hole is reworked if the difference between the diameter and/or area of the hole and the diameter and/or area of the nominally acceptable hole is larger than a pre-determined rework tolerance of the diameter and/or area.

The pre-determined rework tolerance may be ±15%.

The method may further comprise the step of measuring a plurality of holes in an array of holes and determining the average difference between measured diameter and/or area of the array of holes and the diameter and/or area of the nominally acceptable hole wherein the hole is one of the array of holes.

The method may further comprise the step wherein the array of holes is rejected if the average difference between the measured diameter and/or area of the array of holes and the diameter and/or area of the nominally acceptable hole is larger than a pre-determined average hole tolerance of the diameter and/or area of the nominally acceptable hole.

The pre-determined average hole tolerance may be ±15%.

The pre-determined average hole tolerance may be ±5%.

The beam may have a diameter in the range from 0.1 to 1 mm. The beam may have a diameter in the range 0.15 to 0.5 mm. Preferably the hole may have a length in the range 2 to 20 mm and particularly 3 to 15 mm.

The method may further comprise varying the diameter of the beam to match the diameter of the hole, for example, to make the beam diameter slightly narrower than the hole diameter.

The method may further comprise varying the brightness of the beam in accordance with the reflectivity of the reflecting surface.

The beam may be a laser beam.

The method may further comprise varying the distance between the lens system and the hole to alter the imaging position within the hole.

A second aspect of the present invention provides an apparatus for inspecting holes in components, the apparatus comprising:
   a telecentric lens system positionable at a near end of a hole with an optical axis of the lens system aligned with the axis of the hole to image the interior of the hole,
   an illumination system for illuminating the interior of the hole, and
   a camera arranged to receive an image of the illuminated interior of the hole from the telecentric lens system;
   wherein the illumination system comprises:
   a light source for producing a beam of parallel light, and
   optics for directing the produced beam through the telecentric lens system along the optical axis thereof, and through the hole, such that the beam reaches the far end of the hole, and is reflected from a surface located at or adjacent the far end of the hole to illuminate the interior of the hole.

Advantageously, the beam of parallel light can pass right through the hole to provide backlighting illumination by reflecting on e.g. a cavity backwall or suitably arranged reflective surface. The telecentric lens system helps to ensure that the beam remains parallel on entry into the hole. Further the cross-sectional shape of the beam can be altered to correspond to the cross-sectional shape of the hole. The apparatus enables holes with partial breakthrough or other anomalies to be identified.

The apparatus may have any one or, to the extent that they are compatible, any combination of the following optional features.

Preferably, the produced beam has a diameter in the range from 0.1 to 1 mm, and more preferably from 0.15 to 0.5 mm. These ranges correspond to the typical diameters of drilled cooling holes in aerospace gas turbine components, such as high pressure turbine blades, nozzle guide vanes and combustors. Preferably, the beam diameter is slightly narrower than that of the hole to be inspected to avoid direct incidence on the sidewall surface of the hole or on the external surface of the component around the near end of the hole.

Preferably, the light source is adapted to allow the diameter of the produced beam to be varied to match the diameter of the hole.

Preferably, the source is adapted to allow the brightness of the produced beam to be varied in accordance with the reflectivity of the reflecting surface. Thus, for a highly reflective surface, the brightness can be reduced, and conversely with a less reflective surface the brightness can be increased.

Conveniently, the beam of parallel light can be a laser beam and the light source can be a laser light source. However, collimation equipment can be used to produce a beam of parallel light from a source that does not naturally produce a parallel beam.

Preferably the apparatus further comprises a system, such as a movable component table or a movable holder for the telecentric lens system, for varying the distance between the lens system and the hole and thereby altering the imaging position within the hole.

Preferably the camera is connected to a computer system for recording and/or analysing the images. For example, the computer system can be programmed with vision software that measures characteristics of an imaged hole, such as hole shape and diameter. The camera can also be connected to a display device for displaying the images.

Thus the method of the first aspect can be performed using the apparatus of the second aspect.

A third aspect of the present invention provides the use of the apparatus of the second aspect for inspecting a hole in a component.

In the first or third aspect, the component can be an aerospace gas turbine engine component, such as a high pressure turbine blade, a nozzle guide vane, a fuel injector or a combustor. The hole can be a cooling hole in such a component. The hole can open at its far end to a cavity within the component, the reflecting surface being a backwall of the cavity adjacent the far end of the hole.

It will be appreciated that the invention is not limited to inspection of aerospace gas turbine engine components but will also be applicable to hole inspection in other industries e.g. inkjet printers and components where apertures are formed using high energy beams or EDM.

Embodiments of the invention will now be described by way of example with reference to the accompanying drawings in which.

Shortcomings of conventional small hole measurement methods at depth can be overcome by illuminating the hole by projecting a narrow, visible light, parallel beam (such as a laser beam) axially through a telecentric lens system and then through the hole, such that the beam provides illumination by reflecting on a cavity backwall or other suitably arranged reflective surface.

Figure 1:
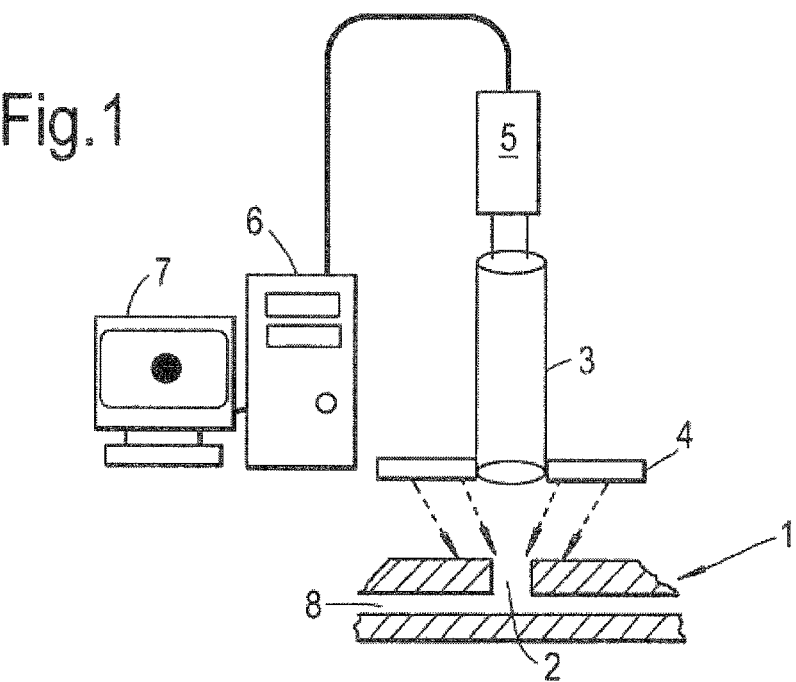
FIG. 1 shows schematically a conventional apparatus for inspecting holes.
Figure 2:
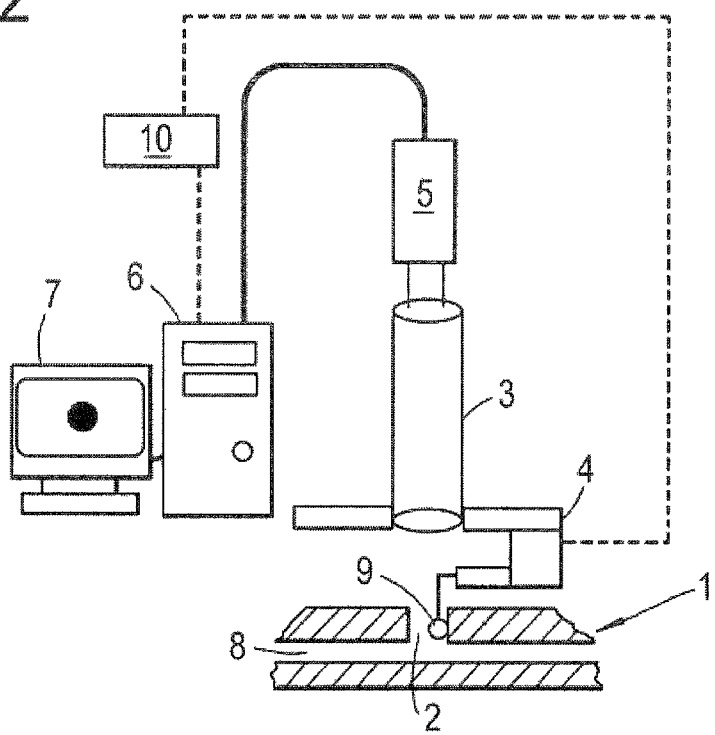
FIG. 2 shows schematically another conventional apparatus for inspecting holes.
Figure 3:
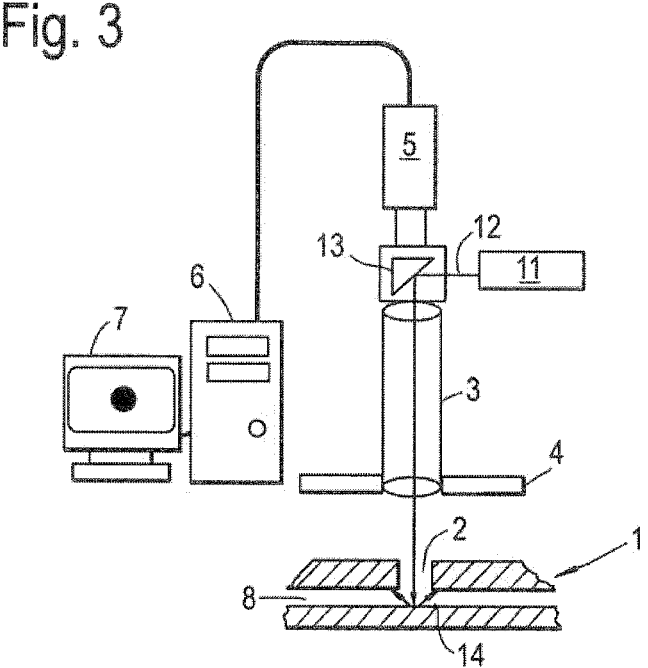
FIG. 3 shows schematically an embodiment of an apparatus for inspecting holes.

FIG. 3 shows schematically an embodiment of an apparatus for inspecting holes. Equivalent features in FIGS. 1 to 3 share the same reference numbers. Thus the system comprises a telecentric lens system 3 positioned above an accessible, exterior end of a hole 2 in a component 1, with the optic axis of the imaging system aligned with the axis of the hole. A camera 5 receives the image obtained by the imaging system and sends the image to a computer 6 running vision software. A monitor 7 can also display the image.

The hole is illuminated with light from a visible light laser source 11. A laser beam 12 emanating from the source is directed to a suitably positioned optical device, such as a half silvered mirror 13, which is arranged to divert the beam along the optical axis of the telecentric lens system 3. Being telecentric, the lens system does not change the diameter or direction of the beam when it emerges from the lens system. The laser beam is narrow compared to the illumination provided by a conventional ring light and thus projects completely through the hole 2, where it reflects from a backwall 14 of the internal cavity 8 to which the hole extends to provide backlighting at the far, internal end of the hole.

The image received by the camera 5 may be analysed to determine a physical parameter such as the diameter, area or other parameter of the hole 2. The image of the illuminated interior of the hole 2 from the telecentric lens system may be measured, either by the use of the monitor 7 or by the vision software, to determine the physical parameter of the hole 2. In the case of the diameter and/or area of the hole 2, the measurement may be compared with the diameter and/or area of a nominally acceptable hole. A difference between the measurement and the parameter of the nominally acceptable hole can then be calculated. In this manner, analysis of the difference between the measured parameters and nominally acceptable parameters may determine whether the hole 2 is within a set or pre-determined tolerance.

It should be appreciated that the hole 2 may not exhibit the properties of a perfect circular cross-section. A diameter of a perfect circle is a straight line segment or chord passing through the centre of the circle. This will be the case for an arrangement in which the cross-section of the hole 2 is a perfect circle. In the case where the hole 2 is not a perfect circle, a diameter of the hole 2 may be defined as a chord across the centre of area of the hole 2 cross-section.

The step of measuring the diameter and/or area of the hole 2 may include measuring more than one diameter of the hole 2. Measuring two or more diameters and then averaging the measurement will determine the average diameter of the hole 2. The average measured diameter of the hole 2 may then be compared in the manner described above to determine the difference between it and the nominally acceptable hole parameter, i.e. is the average measured diameter within the pre-determined tolerance. Including this step will reduce the likelihood of a single diameter of hole 2 being within the pre-determined tolerance in spite of the hole 2 having a distorted and unacceptable shape. For example, the hole 2 may have an elongated shape rather than the desired circular cross-section. In this case it would still be possible to measure a single diameter falling within the pre-determined tolerance of the nominally acceptable hole. Measuring more than one diameter will avoid the hole 2 being passed as acceptable in this situation.

Where two diameters of the hole 2 are measured it may be prudent to perform the measurements on line segments that are perpendicular to each other. Additionally, to improve the accuracy of the average hole diameter, ten or more such measurements may be taken for the hole 2. Depending n processing and measuring times, it may be worthwhile to take as many measurements as are necessary, for example, approximately fifty individual diameter measurements taken at equally spaced angular steps about the centre or centre of area of the hole 2. Each 'diameter' measurement line, or axis, being clocked, at a pre-determined angle, around the centre of area. It should be appreciated that where a number of 'diameter' measurements are taken, the shape of the hole 2 is effectively being determined and verified. Thus for any given expected shape each measured diameter may be compared to a nominal parameter.

Where the image of the individual hole 2 is measured to determine its diameter or area, the difference between the diameter or area of the nominally acceptable hole and the measured diameter or area of the hole 2 may be compared with an acceptable tolerance. This may, of course, be determined for any suitable parameter of the hole 2. The acceptable tolerance is based on the nominally acceptable hole diameter and/or area. For instance, the hole 2 may be rejected when the difference is outside a set or pre-determined rejection tolerance based on the nominally acceptable hole. Alternatively, the hole 2 may be reworked when the difference is outside a set or pre-determined rework tolerance. In the case of reworking the hole 2, the hole 2 may be subjected to the method of measurement again and the new image of the hole 2 analysed in the same manner as described above.

The pre-determined or acceptable tolerances, whether the pre-determined rejection or the pre-determined rework tolerance, may allow for positive and negative deviation from the acceptable parameter, such as diameter and/or area. This means the acceptable tolerances will allow, for example, a hole 2 both larger and smaller in diameter or area than the nominally acceptable hole diameter or area. The pre-determined rejection tolerance may be, for instance, ±20% of the nominally acceptable hole parameter. However, the pre-determined rejection tolerance may also be much tighter or restrictive. For example, the pre-determined rejection tolerance may be of the order of ±15%, ±10% or even ±5%. Similarly, the pre-determined rework tolerance may be, for instance, ±15% of the nominally acceptable hole parameter. The pre-determined rework tolerance may also be much tighter, for example, of the order of 12.5%, ±10% or ±5%. The accuracy of the tolerance will depend on the component's sensitivity to off-nominal flows through the hole 2 bearing in mind its purpose, location and relationship with other holes on the component and/or relative to other holes in its array of holes.

The image received by the camera 5 may also be analysed to determine the physical parameter for an individual hole 2 as one of an array of holes in a component. As laid out above, the parameter, such as the diameter and/or area of the hole 2, may be measured from the image of the illuminated interior of the hole 2. In the case of the diameter or area, for example, the difference between the measured value and the nominally acceptable hole parameter can then be calculated. Thus, for the array of holes, an average difference between the measured parameters for each hole in the array, of which the hole 2 is one, and the nominally acceptable hole parameter, can be calculated from aggregate difference of all the holes in the array.

By way of example, where the average difference is between the measured diameter and/or area, for each hole in the array, and the nominally acceptable hole diameter and/or area, the average difference may be compared with an acceptable average hole tolerance. Again, the acceptable average hole tolerance is based on the nominally acceptable hole diameter and/or area. This may, of course, be possible with other measureable parameters exhibited by the hole 2 and the array of holes. Where the array of holes exhibits an average difference between the measured parameters and the parameters of the nominally acceptable hole outside of the acceptable or pre-determined average hole tolerance, the component defining those holes may required the array of holes to be reworked. Alternatively, the component and array of holes are rejected or scrapped entirely.

The pre-determined or acceptable average hole tolerance may allow for positive and negative deviation from the acceptable average parameter. The pre-determined average hole tolerance may be, for instance, ±15% of the nominally acceptable hole parameter. For example, the allowable difference between the averaged measured diameters of the array of holes and the nominally acceptable hole diameter may be ±15% of the nominally acceptable hole diameter. The predetermined average hole tolerance may be tighter, having a value of, for example, ±10% or ±5%. Generally, the overall average diameter tolerance should be quite tight, but individual hole tolerances could be slacker. This is important where a total flow of coolant is desired.

The reason for a tighter tolerance will be driven by the type of component and therefore how close to the nominally acceptable hole parameters the hole 2 is required to be. In the case of gas turbine engines, where cooling holes are required in the turbine blades or vanes, the tolerance may be determined by the amount of cooling air required to pass through the array of holes. The array of holes may provide the total cooling air for the blade or vane and have an appropriate associated tolerance. Alternatively, the array of holes and associated tolerance to which it refers may provide only a portion of the total cooling air of the blade. The portion of the total cooling may be a specific region on the blade or vane. Controlling the tolerance of the cooling airflow is important to ensure the maintenance of the correct thermal gradient in the blade or vane during operating conditions.

The tolerance associated with the array of holes may depend on the blade or vane location in the turbine module of the engine. For example, a gas turbine engine having low and high pressure turbine stages in the turbine module may have a different cooling airflow tolerance through the turbine blades in each respective stage. This means that the low pressure turbine blades may allow a larger tolerance, relative to the high pressure turbine blades, for both individual hole 2 airflows and the overall airflow through the array of holes. Tolerances on the allowable airflow through the hole 2 and the array of holes correspond to the respective tolerances for measurements such as diameter and/or area.

The level of laser illumination can be controlled, e.g. dependent on the reflecting characteristics of the backwall 14, to provide sufficient light for the camera and vision software without creating excessive glare. Also the diameter of the laser beam 12 can be controlled such that the beam is slightly narrower than the hole. Indeed, the cross-sectional shape of the beam can be varied to match the cross-sectional shape of e.g. a non-circular hole.

To change the focus position within the hole, the distance between the component 1 and the telecentric lens system 3 can be changed. For example, the component may be located on a table which is movable in the direction of the optical axis of the lens system. Alternatively or additionally, the lens system itself may be movable in this direction.

This ability to focus in different positions within the hole 2 allows the measurement of parameters, such as diameter and/or area, of the hole 2 at different positions within the hole 2. This is important because the determining feature may not occur at either the near, or far, end of the hole, but at a position somewhere between the two positions. The determining feature, as to whether to accept or reject the hole 2 relative to an associated nominal feature, may be the diameter or area of the hole 2.

The use of the apparatus enables holes with partial breakthrough or other anomalies to be identified, even if those anomalies are at the far end of the hole.

Breakthroughs and anomalies may be identified using the measured diameter and/or areas of the hole 2. If a large range of diameters is measured at different radial positions around the hole 2, it may be possible to calculate the difference between the shape of the hole 2, based on the measured diameters, and an ideal shape referenced by a similar range of diameters. Such an analysis will most likely be undertaken with appropriate image analysis software.

Figure 4:
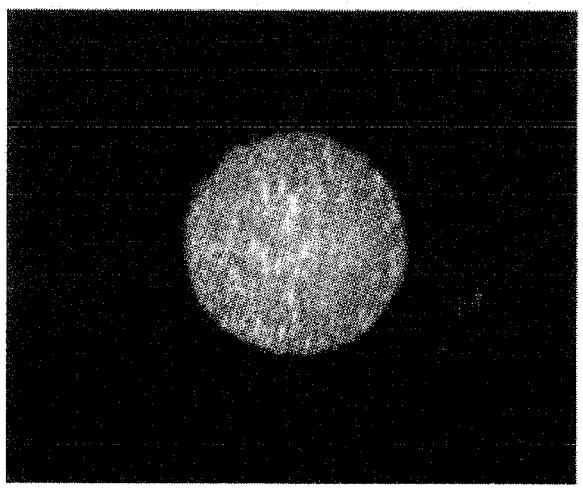
FIG. 4 shows an image of the far end of a backlit 0.36 mm diameter hole.

FIG. 4 shows an image of the far end of a 0.36 mm diameter hole obtained with an apparatus such as the one described above in relation to FIG. 3, the hole extending from the external surface of a component to a cavity within the component. The image is focused at the far end of the hole and allows the breakthrough condition and diameter of the hole at that end to be determined. The central brightness is the reflection from the backwall of the cavity.

Figure 5:
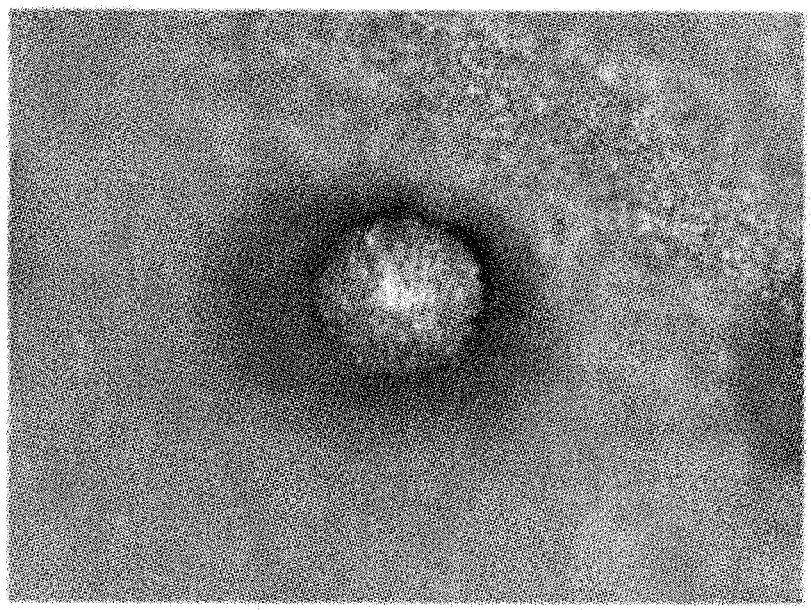
FIG. 5 shows an image of the far end of a backlit hole but with top lighting also applied.

FIG. 5 shows a similar image of the hole, but this time with top lighting applied to illuminate the external surface of the component around the near end of the hole. The image demonstrates that the focus is indeed on the far end of the hole and not the near end.

The need to measure or verify the diameter, shape or breakthrough condition of small holes is common in manufacturing industry (e.g. cooling holes in a turbine blade, a nozzle guide vane, a fuel injector or a combustor). The approach of combining parallel beam illumination and a vision system equipped with a telecentric lens system, whereby the parallel beam provides backlighting, facilitates a relatively fast, non-contact inspection method for such holes.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A method of inspecting at least one hole in a component, the method comprising:
   positioning a telecentric lens system at a near end of a hole with an optical axis of the lens system aligned with an axis of the hole,
   directing a beam of parallel light through the telecentric lens system along the optical axis thereof and through the hole such that the beam reaches a distal end of the hole and is reflected from a surface located at or adjacent the distal end of the hole to illuminate the interior of the hole,
   receiving an image of the illuminated interior of the hole from the telecentric lens system,
   measuring at least one diameter and/or an area of the hole from the image of the illuminated interior of the hole and
   determining the difference between the measured diameter and/or area of the hole and a diameter and/or area of a nominally acceptable hole.

2. The method of claim 1 wherein the step of measuring the diameter and/or an area of the hole comprises measuring two or more diameters of the hole and determining the average of the two or more diameters of the hole.

3. The method of claim 1 wherein the hole is rejected if the difference between the diameter and/or area of the hole and the diameter and/or area of the nominally acceptable hole is outside a pre-determined rejection tolerance of the diameter and/or area of the nominally acceptable hole.

4. The method of claim 3 wherein the pre-determined rejection tolerance is ±20% of the diameter and/or area of the nominally acceptable hole.

5. The method of claim 1 wherein the hole is reworked if the difference between the diameter and/or area of the hole and the diameter and/or area of the nominally acceptable hole is outside a pre-determined rework tolerance of the diameter and/or area of the nominally acceptable hole.

6. The method of claim 5 wherein the pre-determined rework tolerance is ±15% of the diameter and/or area of the nominally acceptable hole.

7. The method of claim 1 wherein the method includes the step of measuring a plurality of holes in an array of holes and determining the average difference between measured diameters and/or areas of the holes in the array of holes and the diameter and/or area of the nominally acceptable hole.

8. The method of claim 7 wherein the array of holes is rejected if the average difference between the measured diameter and/or area of the array of holes and the diameter and/or area of the nominally acceptable hole is outside a pre-determined average hole tolerance of the diameter and/or area of the nominally acceptable hole.

9. The method of claim 8 wherein the pre-determined average hole tolerance is ±15% of the diameter and/or area of the nominally acceptable hole.

10. The method of claim 8 wherein the pre-determined average hole tolerance is ±5% of the diameter and/or area of the nominally acceptable hole.

11. The method according to claim 1, wherein the beam has a diameter in the range from 0.1 to 1 mm.

12. The method according to claim 1 further comprising varying the diameter of the beam to match the diameter of the hole.

13. The method according to claim 1 further comprising varying the brightness of the beam in accordance with the reflectivity of the reflecting surface.

14. The method according to claim 1, wherein the beam is a laser beam.

15. The method according to claim 1 further comprising varying the distance between the lens system and the hole to alter the imaging position within the hole.

16. An apparatus for inspecting holes in components, the apparatus comprising:
a telecentric lens system positionable at a near end of a hole with an optical axis of the lens system aligned with the axis of the hole to image the interior of the hole,
an illumination system for illuminating the interior of the hole, and
a camera arranged to receive an image of the illuminated interior of the hole from the telecentric lens system;
wherein the illumination system comprises:
a light source for producing a beam of parallel light, and
optics for directing the produced beam through the telecentric lens system along the optical axis thereof, and through the hole, such that the beam reaches the far end of the hole, and is reflected from a surface located at or adjacent the far end of the hole to illuminate the interior of the hole.

17. An apparatus according to claim 16, wherein the light source is adapted to allow the diameter of the produced beam to be varied to match the diameter of the hole.

18. An apparatus according to claim 16, wherein the light source is adapted to allow the brightness of the produced beam to be varied in accordance with the reflectivity of the reflecting surface.

19. An apparatus according to claim 16, wherein the beam of parallel light is a laser beam and the light source is laser light source.

20. An apparatus according to claim 16 further comprising a system for varying the distance between the lens system and the hole to alter the imaging position within the hole.

* * * * *